United States Patent [19]

Maeyama et al.

[11] Patent Number: 4,702,904

[45] Date of Patent: * Oct. 27, 1987

[54] ORAL COMPOSITION CONTAINING ZIRCONIUM-BONDED SYNTHETIC AMORPHOUS SILICATE

[75] Inventors: Tsutomu Maeyama, Chiba; Kenji Kaneko; Shigeru Ishii, both of Tokyo, all of Japan

[73] Assignee: Lion Corporation, Tokyo, Japan

[*] Notice: The portion of the term of this patent subsequent to Apr. 29, 2003 has been disclaimed.

[21] Appl. No.: 800,143

[22] Filed: Nov. 20, 1985

[30] Foreign Application Priority Data

Dec. 28, 1984 [JP] Japan ................................ 59-277810

[51] Int. Cl.$^4$ .......................... A61K 7/18; A61K 7/16
[52] U.S. Cl. ...................................... 424/52; 424/57; 424/58
[58] Field of Search ........................................... 424/52

[56] References Cited

U.S. PATENT DOCUMENTS

3,541,017  11/1970  Muhler ................................ 525/140
4,397,837  8/1983   Raaf et al. ............................ 424/51
4,585,648  4/1986   Maeyama et al. .................... 424/49

FOREIGN PATENT DOCUMENTS

0046371  3/1974  Australia .

OTHER PUBLICATIONS

Manahan, *General Applied Chemistry*, Willard Grant Press, Boston, Mass., 1978, pp. 41–42.

*Primary Examiner*—J. R. Brown
*Assistant Examiner*—F. T. Moezie
*Attorney, Agent, or Firm*—Birch, Stewart, Kolasch & Birch

[57] ABSTRACT

An oral composition which comprises containing therein synthetic amorphous zirconosilicate containing 0.1 to 10 wt % of zirconium in terms of $ZrO_2$ based on $SiO_2$ and a fluoride compound. The fluoride compound is retained stable for a long period of time.

14 Claims, 3 Drawing Figures

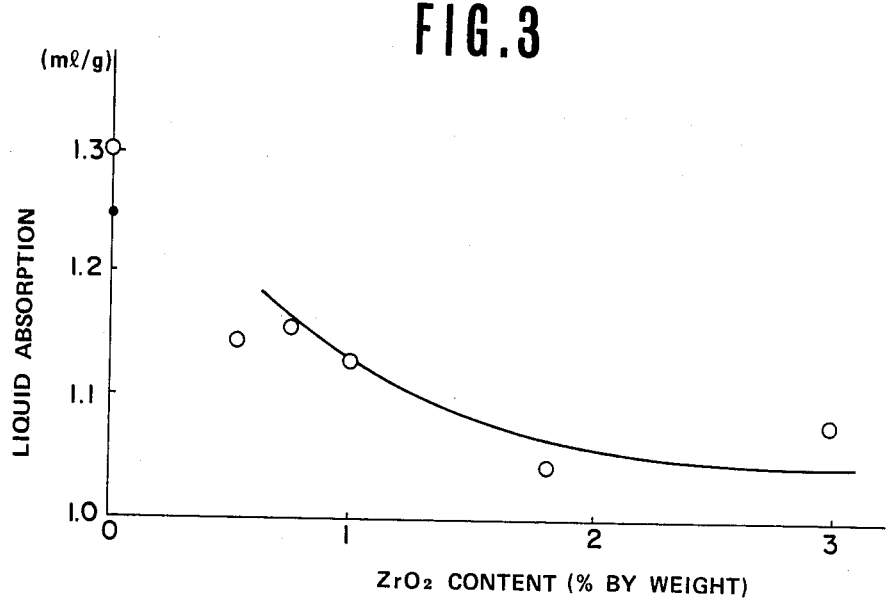

ORAL COMPOSITION CONTAINING ZIRCONIUM-BONDED SYNTHETIC AMORPHOUS SILICATE

BACKGROUND OF THE INVENTION

1. Field of the Invention:

The present invention relates to an oral composition comprising a fluoride compound. More particularly, it relates to an oral composition which is effective for prevention of dental caries because it permits a fluoride compound contained therein to maintain its stability for a long period of time and to give a high uptake of fluoride to the tooth enamel.

2. Description of the Prior Art:

It has been common practice to inhibit dental caries by using an oral composition such as dentifrice with a fluoride compound such as sodium fluoride, sodium monofluorophosphate, and stannous fluoride, contained therein which permits uptake of fluoride by tooth enamel for tooth reinforcement.

It is soluble fluoride dissolved in the composition that effectively acts on the tooth enamel. A fluoride compound initially incorporated into the composition may react with other ingredients in the composition to become insoluble. In this case, the amount of effective soluble fluoride decreases in the composition and the amount of fluoride for uptake by the tooth enamel will also decrease.

Usually a dentifrice contains calcium secondary phosphate, calcium carbonate, or aluminum hydroxide as an abrasive. When a dentifrice containing such a calcium-based or aluminum-based abrasive is incorporated with sodium fluoride or stannous fluoride, the fluoride ions react with calcium ions or aluminum ions liberated from the abrasive. This reaction forms insoluble $CaF_2$ or $AlF_3$ and deactivates the fluoride compound incorporated in the composition. This disadvantage is overcome to some extent when a monofluorophosphate is used as a fluoride compound; but deactivation is still inevitable where the storage period is long.

There has been a demand for a new abrasive to place the calcium-based or aluminum-based abrasives which are poor in miscibility with a fluoride compound. The new abrasive is required to be miscible with a fluoride compound, have good cleaning power, taste, and storage stability so that it would be suitable for use in oral compositions such as dentifrice.

SUMMARY OF THE INVENTION

Therefore, it is an object of the present invention to provide an oral composition containing a fluoride compound in which the fluoride compound retains its stability for a long period of time, thereby giving to the tooth enamel, a high uptake of fluoride even after the oral composition had been subjected to a long storage period.

According to the present invention, there is provided an oral composition which comprises a zirconium-bonded synthetic amorphous silicate (zirconosilicate) containing 0.1 to 10% by weight of zirconium in terms of $ZrO_2$ based on $SiO_2$ and a fluoride compound.

The synthetic amorphous zirconosilicate containing 0.1 to 10% by weight of zirconium in terms of $ZrO_2$ based on $SiO_2$ has excellent properties as an abrasive for dentifrices, i.e. said abrasive has an adequate degree of cleaning power, good taste and superior storage stability. It is also suitable as an abrasive for a transparent toothpaste.

The present inventors have also found that zirconosilicate is highly miscible with fluoride compounds, an oral composition containing the zirconosilicate permits a fluoride compound contained therein to remain stable for a long period of time, with the maximum retention of fluoride activity and the minimum deactivation of effective fluoride. Where such composition is used, the uptake of fluoride by the tooth enamel is high. Moreover, in the case of a composition containing stannous ions or a composition containing stannous ions and myoinositol phosphate ester in addition to fluoride ions, a synergistic effect is produced and the effect of active fluoride is ensured. Therefore, an oral composition is very effective for the prevention of dental caries if it comprises a synthetic amorphous zirconosilicate containing 0.1 to 10% by weight of zirconium in terms of $ZrO_2$ based on $SiO_2$ and a fluoride compound. The present invention was completely based on these findings.

By reading the following description taken in conjuction with the acompanying drawings, the above and other objects, features, and advantages of the present invention will be more fully understood.

BRIEF DESCRIPTION OF THE DRAWINGS

FIG. 3 is a graph showing the liquid absorption of the zirconosilicate.

DETAILED DESCRIPTION OF THE INVENTION

Figure 1:
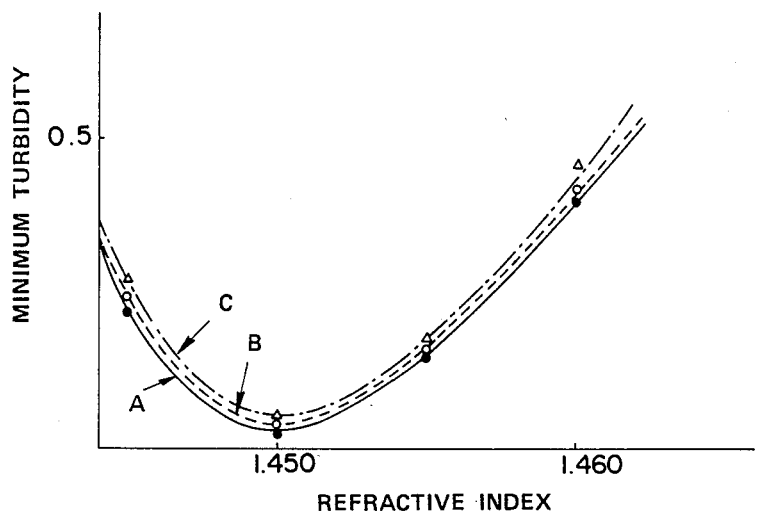
FIG. 1 is a graph showing the change in the transparency at various refractive indexes in the case where toothpaste compositions using zirconosilicates as the abrasive are stored under various condition.

In the oral composition according to this invention, a zirconium-bonded synthetic amorphous silicate (zirconosilicate) having a zirconium content of 0.1 to 10% by weight as $ZrO_2$ based on $SiO_2$.

The oral composition containing the zirconosilicate as an abrasive shows an excellent storage-stability, i.e. a good shape retention and less syneresis even after a long-term storage at a high temperature. Moreover, in the case of using the zirconosilicate as an abrasive for a transparent dentifrice composition, the zirconosilicate shows less change in the refractive index even after a long-term storage, and hence maintains the transparency of the dentifrice composition even during a long-term storage or storage in cold or warm districts, resulting in providing a transparent dentifrice composition which is excellent in the stability of the transparency.

Further, the zirconosilicate having an aimed liquid absorption may be used singly or mixed with the other abrasives to obtain a dentifrice composition which has an adequate viscosity and can be extruded with ease from a container.

The zirconosilicate used in this invention contains zirconium bonded with $SiO_2$ usually as the form of $ZrO_2$ and is different from mere mixtures of anhydrous silica with zirconium dioxide or zirconyl hydroxide, and crystalline zirconium silicate.

It is preferred that the SiO$_2$ content in the zirconosilicate is more than 70% by weight and, particularly, more than 85% by weight of the anhydrous matter (zirconosilicate dried at 105° C. for 2 hours). The zirconium content in the zirconosilicate is in the range of 0.1 to 10% by weight, more preferably, 0.2–2% by weight as ZrO$_2$ based on SiO$_2$ in view of the liquid absorption, stability for transparency and abrasing power. If the zirconium content is less than 0.1% by weight as ZrO$_2$, no substantial advantage of using the zirconosilicate can be obtained. On the contrary, if the zirconium content is more than 10% by weight as ZrO$_2$, control for the physical properties thereof is difficult, which may be undesired as for the transparent dentifrice abrasive.

The zirconosilicate may contain aluminum, magnesium, sodium, potassium, lithium, hafnium, etc. dispersed or bonded therein, which may possibly be introduced as impurities from sodium silicate, zirconyl chloride, sulfuric acid or the like as the starting material for the zirconosilicate. It is preferred that the content of the impurities is less than 10%, by weight of the zirconosilicate.

Further, the amount of adsorbed water to the zirconosilicate may be less than 20% at 25° C. and 70% RH (relative humidity).

It is preferred that the zirconosilicate for use in this invention has a refractive index of 1.40 to 1.47, a specific surface area of less than 800 m$^2$/g, a specific gravity of 1.9 to 2.3 and a liquid absorption of 0.4 to 2.0 ml/g as measured by the methods shown in Examples to be described later.

Furthermore, the zirconosilicate to be used as the abrasive preferably has an average particle size of less than 0.5 μm when measured by the SEM (scanning electron microscope) method and an average particle size of 1–30 μm, particularly 2–20 μm when measured by the sedimentation method.

The amount of the zirconosilicate blended into a dentifrice composition may preferably be in the range of 1 to 50% by weight and, more preferably, 5 to 30% by weight based on the total weight of the composition.

The zirconosilicate as described above can be obtained, for instance, through a reaction of a mineral acid containing a zirconium salt with an alkali metal salt of silicic acid. The alkali metal salt of silicic acid may include sodium, potassium and lithium silicates, sodium silicate being preferred in view of its relatively inexpensive cost. The alkali metal salt of silicic acid may preferably have a molar ratio (SiO$_2$/X$_2$O, X$_2$O, where X represent alkali metal) between 2 to 4. The mineral acid for acidifying the alkali metal silicate includes, for instance, hydrochloric acid, sulfuric acid and nitric acid.

In the case of preparing the zirconosilicate through the reaction of alkali metal silicate and mineral acid, it is necessary to add a zirconium salt. The zirconium salt usable herein includes preferably water-soluble zirconium salt, for example, zirconyl chloride (ZrOCl$_2$), zirconyl sulfate, zirconyl acetate, etc. In this case, it is most suitable to previously add a zirconium salt to mineral acid, and then react the alkali metal silicate therewith.

The foregoing step is very much effective because zirconosilicates of various levels of abrasing power and liquid absorption can be produced depending on the zirconium content and, accordingly, the abrasing power and the liquid absorption can be adjusted with ease.

According to this invention, the oral composition containing the above-mentioned zirconosilicate is incorporated further with a fluoride compound. The combination of zirconosilicate and fluoride compound permits the active fluoride in the composition to remain stable for a long period of time and ensures the uptake of fluoride by the tooth enamel.

Preferred examples of the fluoride compound include alkali metal fluorides (such as sodium fluoride, potassium fluoride, lithium fluoride, and ammonium fluoride), alkali metal monofluorophosphates (such as sodium monofluorophosphate, sodium hydrogen monofluorophosphate, potassium monofluorophosphate, and ammonium monofluorophosphate), potassium hexafluorozirconate, potassium hexafluorotitanate, and stannous-containing fluoride compounds (such as stannous fluoride, and stannous chlorofluoride). They may be used alone or in combination with one another. Additional examples that can be used include cesium fluoride, aluminum fluoride, copper fluoride, lead fluoride, iron fluoride, nickel fluoride, zirconium fluoride, silver fluoride, hexylamine hydrofluoride, lauroylamine hydrofluoride, cetylamine hydrofluoride, glycine hydrofluoride, lysine hydrofluoride, and alanine hydrofluoride.

According to this invention, the content of the fluoride compound in the oral composition may be 50 to 10000 ppm, preferably 200 to 10000 ppm in terms of fluoride. For dentifrice composition, the amount of total fluoride should preferably be 1000 ppm or less.

Where a stannous-containing fluoride compound (such as stannous fluoride or stannous chlorofluoride) is selected from the above-mentioned fluoride compounds, or where a stannous compound is incorporated to the stannous-free fluoride compound, the effect of reinforcing teeth is produced by the stannous ions. Where myo-inositol phosphate ester or a salt thereof is incorporated in addition to fluoride ions and stannous ions, the amount of fluoride uptake by the tooth enamel is increased. This leads to a marked effect of preventing dental caries.

The myo-inositol phosphate ester that can be used is one which is produced by esterifying 1 to 6 hydroxyl groups in myo-inositol with phosphoric acid. Preferred examples are myo-inositol tetraphosphate ester, myo-inositol pentaphosphate ester, and myo-inositol hexaphosphate ester produced by esterifying 4 to 6 hydroxyl groups with phosphoric acid, respectively. The salt of myo-inositol phosphate ester that can be used is one which is formed by substituting some or all of hydrogen atoms in the phosphate group with metals. The salts includes sodium salt, potassium salt, ammonium salt, calcium salt, magnesium salt, aluminum salt, and barium salt. Preferable among them are penta- and hexa-sodium salt, penta- and hexa-potassium salt, tetracalcium salt, pentamagnesium salt, and pentabarium salt. Double salts may also be used. Preferred examples of such salts are highly soluble alkali metal salts and ammonium salts. The myo-inositol phosphate ester and salt thereof may be used individually or in combination with one another.

The myo-inositol phosphate ester and salt thereof may be incorporated in an amount of 0.5% and above, preferably 0.1 to 20%, more preferably 0.2 to 10% by weight based on the total weight of the composition. The molar amount of the myo-inositol phosphate ester or salt thereof may be 0.01 to 4 mol, preferably 0.02 to 3 mol, more preferably 0.03 to 2.5 mol for 1 mol of stannous ions dissolved in the composition.

As mentioned above, the myo-inositol phosphate ester or salt thereof is effective in a composition containing fluoride and stannous ions. Where the fluoride compound is not a stannous compound, it is possible to add a stannous compound separately. The stannous compound for this purpose may be a water-soluble stannous compound or a sparingly water-soluble stannous compound or a combination thereof. Preferred examples of the water-soluble stannous compound include stannous chloride, stannous acetate, stannous sodium fluoride, stannous potassium fluoride, stannous hexafluorozirconate, stannous sulfate, stannous tartrate, and stannous gluconate. They may be used individually or in combination with one another. Preferred examples of the sparingly water-soluble stannous compound include stannous pyrophosphate, stannous metaphosphate, stannous oxide, stannous oxalate, and stannous phosphate. They may be used individually or in combination with one another.

The content of stannous ions in the composition should be 0.03% and above, preferably 0.1% by weight and above. There is no upper limit to the content of the stannous compound. A portion of the stannous compound incorporated may be present in the form of precipitates or in the undissociated state. The amount of solubilized stannous ions may be less than 7%, preferably less than 5% by weight in the composition. Where a soluble stannous compound and a sparingly soluble stannous compound are used together, the amount of the former may be 0.03% and up, preferably 0.1% by weight and up in terms of tin in the composition, and the amount of the latter may be 0.2 to 10% by weight in terms of tin in the composition. The soluble stannous compound is the main source that supplies dissolved stannous ions; and the precipitates of the sparingly soluble stannous compound serves as a reservoir that keeps dissolved active stannous ions at a constant level for a long period of time.

The oral composition may be prepared and applied in the form of dentifrice such as toothpaste. It may be incorporated with, in addition to the ingredients of this invention, proper ingredients according to the type of the oral composition.

Where the oral composition is used as dentifrice, it is prepared by incorporating a vehicle composed mainly of water, humectant, and flavor, with zirconosilicate and fluoride compound, and optionally a myo-inositol phosphate ester and stannous compound. Where transparent dentifrice is required, the vehicle is formulated transparent so that it has the same refractive index as that of zirconosilicate. The thus obtained transparent dentifrice composition may keep its transparency for a long time at various storage temperatures because the zirconium-bonded synthetic amorphous silicate shows less change in the refractive index and maintains the substantial identity of the refractive index with that of the vehicle even after a long-term storage.

The humectant usable herein includes one or more of glycerine, sorbitol, polyethylene glycol of an average molecular weight of 200 to 6000, ethylene glycol, propylene glycol, reducing starch sugar, xylytol, etc. which may be blended by in an amount of 10 to 80%, preferably 30 to 60% by weight based on the total weight of the composition.

The vehicle contains one or more flavours including essential oils such as peppermint and spearmint, flavour materials such as l-menthol, carvone, eugenol, anethole, etc. The blending amount thereof is usually 0.1 to 5%, preferably 0.5 to 2% by weight of the composition.

Furthermore, a sweetening agent such as sodium saccharine, asparzyme, stevioside, neohesperidyldihydrochalcone, glycyrrhizin, perillartine, p-methoxycinnamic aldehyde, etc. may be blended singly or in combination with the blending amount usually between 0 to 5%, preferably 0.01 to 5%, more preferably 0.05 to 2% by weight of the composition.

The vehicle may be incorporated as desired with one or more of binders which include carrageenan, sea weed extracts, cellulose derivatives such as sodium carboxymethylcellulose, alkali metal alginates such as sodium alginate, gums such as xanthane gum, synthetic binders such as polyvinyl alcohol, carboxyvinyl polymers (e.g., Carbopol (registered trade mark)), and polyvinyl pyrrolidone, inorganic binders such as gelling amorphous anhydrous silica, Veegum (registered trade mark), kaoline, bentonite, etc. The binder may be blended in an amount of 0 to 5% and, particularly 0.1 to 5% by weight of the total weight of the composition. Among them, sodium carboxymethylcellulose, carrageenan and carboxyvinyl polymers are preferred. Particularly, sodium carboxymethylcellulose having the eterification of 1.1 or more and the viscosity of 1% aqueous solution of 100 centipoises or less can preferably be used. As carrageenan, $\iota$-carrageenan and $\kappa$-carrageenan are preferred. When $\iota$-carrageenan is used, a water-soluble calcium salt is preferably used in combination. When $\kappa$-carrageenan is used, a water-soluble potassium salt is preferably used in combination.

The dentifrice vehicle may be blended as required with one or more of surfactants including anionic surfactants such as water-soluble salt of higher alkyl sulfates having 8 to 18 carbon atoms in the alkyl group (for example, sodium lauryl sulfate and sodium myristyl sulfate), $\alpha$-olefin sulfonates (for example, sodium $\alpha$-olefin sulfonate having 14 carbon atoms), 2-hydroxy alkane sulfonates, water-soluble salts of higher fatty acid monoglyceride sulfonates having 10 to 18 carbon atoms in the fatty acid group (for example, sodium lauryl monoglyceride sulfonate and sodium coconuts monoglyceride sulfonate), higher fatty acid sodium monoglyceride monosulfates, condensed products of higher fatty acids having 12 to 18 carbon atoms and amino acids and their derivatives (for example, sodium-N-methyl-N-palmitoyl tauride, sodium-N-lauroyl-sarcosinate, sodium-N-lauroyl-$\beta$-alanine, sodium-N-long chain acyl amino acids, etc.), as well as nonionic surfactants such as alkyloyl diethanol amides having 10 to 16 carbon atoms in the fatty acid group, stearyl monoglyceride, sucrose fatty acid esters having 12 to 18 carbon atoms in the fatty acid group (for example, sucrose mono- and di-laurate), lactose fatty acid esters, lactitol fatty acid esters, maltitol fatty acid esters, polyoxyethylene (60 moles) sorbitan monostearate, polymers of ethylene oxide and propylene oxide and the derivatives thereof (for example, polyoxyethylene polyoxypropylene monolauryl ester), etc. These nonionic surfactants may preferably be used in combination with condensed products of higher fatty acids and amino acids. The blending amount of the surfactant is usually 0 to 5%, preferably 0.1 to 5%, more preferably 0.5 to 2%.

There may be further added preservatives such as sodium dihydroacetate, p-hydroxymethyl benzoic acid, p-hydroxyethyl benzoic acid, p-hydroxybutyl benzoic acid and sodium benzoate, etc., microcrystalline cellulose powders such as Avicel (Trade Mark), gelatine, and the other ingredients. The dentifrice vehicle may also contain one or more effective ingredients which include enzymes such as dextranase, amylase, protease, mutanase, phosphatase, lysozyme and lytic enzyme, chlorhexydine salts such as chlorhexydine hydrochloride and chlorhexydine gluconate, sodium copper chlorophyllin, hinokitiol, ε-aminocaproic acid, tranexamic acid, ethane dihydroxydiphosphonate, allantoin chlorohydroxy aluminum, dihydrocholesterol, glycyrrhizin, glycyrrhizinic acid, azulene, extracts of herbs such as chamomile, chlorophyl, chelating phosphoric acid compounds such as glycelophosphate, sodium chloride and water-soluble inorganic phosphoric acid compounds in an effective amount.

Furthermore, in addition to the zirconosilicate, the other abrasives and polishing agents including amorphous anhydrous silica, aluminosilicate, calcium secondary phosphate dihydrate, calcium secondary phosphate anhydrate, calcium carbonate, insoluble sodium metaphosphate, aluminum hydroxide, alumina, polymethyl methacrylate, crystalline zirconium silicate, titanium dioxide, etc. may be blended within the limits over which the effect of the invention will be harmed. Where the calcium-based or aluminum-based abrasive is additionally blended, its content should preferably be less than 10% by weight of the total weight of the composition because the calcium-based or aluminum-based abrasive tends to deactivate a fluoride compound. In the case of preparing a transparent dentifrice composition by using the zirconosilicate, the abrasives ordinarily used for transparent dentifrices such as amorphous anhydrous silica and aluminosilicate, and the abrasives and the polishing agents tending to decrease the transparency of the transparent dentifrice composition may also be blended. However, the abrasive and the polishing agent tending reduce the transparency are blended by the amount preferably less than 10% by weight of the total weight of the composition and, more preferably, less than 10% by weight of the zirconosilicate. Further, the zirconosilicate having an aimed liquid absorption may be mixed with the above-described abrasive to obtain an opaque toothpaste composition that has an adequate viscosity and can be extruded with ease from a tubular container.

The oral composition of this invention is not specifically limited in pH. At pH 4.6 to 9.5, preferably at pH 5 to 8, the retention of active fluoride is improved and the uptake of fluoride by the tooth enamel is also improved.

The oral composition of the invention contains a fluoride compound and zirconosilicate which is highly miscible with the fluoride compound. On account of this combination, the active fluoride in the composition is kept stable for a long period of time. Thus the composition permits the effective uptake of fluoride by the tooth enamel. Further, on account of the use of the zirconosilicate, the oral composition of this invention keeps its shape without syneresis even after long storage at a high temperature. Where this zirconosilicate is used as an abrasive for transparent toothpaste, it remains almost unchanged in refractive index, which is substantially equal to that of vehicle, even after long storage at low or high temperatures. This means that the transparent toothpaste remains transparent for a long time. If the zirconosilicate having the desired liquid absorption is used alone or in combination with other abrasives, it is possible to produce a toothpaste composition which has a proper viscosity and yet can be readily extruded from its container.

The following examples will further illustrate the practice of the present invention particularly when taken in conjunction with comparative examples. They are given by way of illustration and are not to be construed as limiting the invention.

[EXAMPLE 1]

Zirconium-bonded synthetic amorphous silicates (zirconosilicates) having various zirconium contents were prepared by the process described below.

Preparation of zirconosilicate

To a 20 liter volume reactor with buffle plates provided with a stirrer having a turbine blade of 150 mm diameter, were charged 10 kg of an aqueous solution of sodium silicate ($Na_2O.3.1SiO_2$) containing 100 g/kg of $SiO_2$ and 20 g/kg of NaCl, and 3688 g of 10% sulfuric acid containing zirconyl chloride at various concentrations were added at the flow rate of 36 g/min while maintaining the reaction temperature at 87° C. Then, 10% sulfuric acid was added at the flow rate of 83 g/min and, when the pH value of the reaction system reached 2.8, the addition of the acid was stopped and the reaction product was aged for 15 min as it was. Thereafter, filtration and water washing were repeated and after drying in a drier kept at 110° C., the product was finely pulverized to obtain zirconosilicate containing various zirconium contents.

Next toothpastes having the following formulation were prepared using zirconosilicate having $ZrO_2$ content of 0.5% by weight based on $SiO_2$ and amorphous anhydrous silica (Zeodent 113 ®), respectively, and they were filled in aluminum-laminated plastic tubes to measure the storage-stability (retention and syneresis). The results are shown in Table 1.

| Toothpaste formulation | |
|---|---|
| Abrasive | 25.0% |
| 96% Glycerine | 10.0 |
| 70% Sorbitol | 32.0 |
| Propylene glycol | 4.0 |
| Sodium carboxymethylcellulose | 1.2 |
| Sodium lauryl sulfate | 1.5 |
| Sodium saccharine | 0.1 |
| Flavour | 1.0 |
| Purified water | balance |
| Total | 100.0% |

TABLE 1

| Abrasive | Item | Immediately after preparation | One month | | | Three months | | |
|---|---|---|---|---|---|---|---|---|
| | | | Room temperature | 40° C. | 50° C. | Room temperature | 40° C. | 50° C. |
| The invention (zircono-silicate) | Shape retention | 3 | 3 | 3 | 3 | 3 | 3 | 3 |
| | Syneresis | 1 | 1 | 1 | 2 | 1 | 2 | 3 |
| Amorphous anhydrous | Shape retention | 3 | 3 | 3 | 2 | 2.5 | 3 | 3.5 |

TABLE 1-continued

| | | Storage condition | | | | | | |
|---|---|---|---|---|---|---|---|---|
| | | Immediately after preparation | One month | | | Three months | | |
| Abrasive | Item | | Room temperature | 40° C. | 50° C. | Room temperature | 40° C. | 50° C. |
| silica | Syneresis | 1 | 1 | 2 | 3 | 2 | 3 | 4 |

From the above results, it is recognized that the toothpaste blended with the zirconosilicate as an abrasive according to this invention has an excellent shape retention and results in less syneresis, and hence is excellent in the storage-stability.

The method of evaluation and the standards thereof for the shape retention and syneresis are as follows.

Shape retention

Method of evaluation

The outer shape of the toothpaste when extruded out of a tube was estimated based on the visual observation according to the following estimation standards.

Estimation standards

Score

5 : Extruded toothpaste keeps the circular shape at the exit of the tube as it is and the mass of paste tends to tumble instably and falls out of a toothbrush.

4 : Extruded toothpaste retains the circular shape of the tube exit at its upper portion while slightly flattens at the bottom.

3 : Extruded toothpaste is in a preferred state for use almost keeping the shape of the tube exit and flattened at the bottom, thus placed stably on a toothbrush.

2 : Extruded toothpaste is soft and loses the circular shape but does not flow into the planted fibers of a toothbrush.

1 : Extruded toothpaste flows into the planted fibers of a toothbrush.

Syneresis

Method of evaluation

The extent of separation of liquid phase in the toothpaste upon extrusion from the tube was estimated on the visual observation according to the following standards.

Estimation standards

Score

1 No liquid separation is recognized at all.

2 : Slight liquid separation is observed at the exit of the tube.

3 : Liquid separation is observed at the exit of the tube, but with no practical problem.

4 : Remarkable liquid separation is observed at the exit of the tube and liquid separation occurs in a viscous appearance throughout the entire portion.

5 : Distinct liquid separation is observed throughout the entire portion.

6 : Out of the standards.

[EXAMPLE 2]

Toothpastes having the formulations shown in Table 2 and Table 3 were prepared using the zirconosilicate having a $ZrO_2$ content of 0.3% by weight based on $SiO_2$ and the amorphous anhydrous silica as the abrasive, respectively, and adjusting their refractive indexes variously. After storing the toothpastes at a predetermined temperature for one month, the turbidity at each of the refractive indexes was measured in the following manner.

Figure 2:
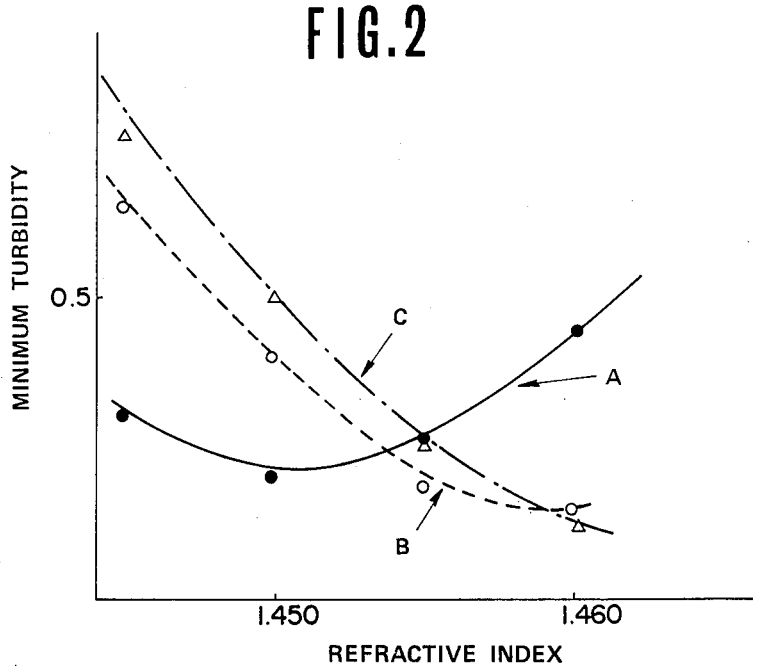
FIG. 2 is a graph showing the change in the transparency at various refractive indexes in the case where toothpaste compositions using amorphous anhydrous silica as the abrasive are stored under various conditions.

FIG. 1 shows the result of the measurement for the turbidity of the toothpastes containing the zirconosilicate and FIG. 2 shows the result of measurement for the turbidity of the toothpastes containing the amorphous anhydrous silica. In the figures, "A" represents the result just after the preparation of the toothpaste, "B" represents the result after one month storage at a room temperature (about 25° C.) and "C" represents the result after one month storage at 50° C.

Measurement of refractive index and turbidity

Glycerine and water were mixed properly to prepare dispersants having various refractive indexes. 15 g of the sample were dispersed into each 35 g of the dispersants and mixed under defoaming in a vacuum stirring crusher for 10 min.

The refractive index and the turbidity for each of the dispersions at 25° C. were measured, and refractive index-turbidity curves were drawn to determine the refractive index of the dispersion at as the minimum turbidity as the refractive index of the sample.

In this experiment, Abbe's refractometer was used for the measurement of the refractive index and an integrating sphere type turbid meter was used for the measurement of the turbidity. The turbidity was determined based on the transparency at 1 mm thickness of the specimen.

TABLE 2

| Formulation | I | II | III | IV |
|---|---|---|---|---|
| Zirconosilicate | 20% | 20% | 20% | 20% |
| 96% Glycerine | 19.9 | 20.8 | 21.8 | 22.7 |
| 70% Sorbitol | 39.7 | 41.7 | 43.6 | 45.5 |
| Polyethylene glycol | 5.0 | 5.0 | 5.0 | 5.0 |
| Sodium carboxymethyl-cellulose | 1.2 | 1.2 | 1.2 | 1.2 |
| Sodium lauryl sulfate | 1.5 | 1.5 | 1.5 | 1.5 |
| Sodium saccharine | 0.1 | 0.1 | 0.1 | 0.1 |
| Flavour | 1.0 | 1.0 | 1.0 | 1.0 |
| Purified Water | 11.6 | 8.7 | 5.8 | 3.0 |
| Total | 100.0% | 100.0% | 100.0% | 100.0% |
| Refractive index of toothpaste | 1.445 | 1.450 | 1.455 | 1.460 |

TABLE 3

| Formulation | V | VI | VII | VIII |
|---|---|---|---|---|
| Amorphous anhydrous silica | 20% | 20% | 20% | 20% |
| 96% Glycerine | 19.9 | 20.8 | 21.8 | 22.7 |
| 70% Sorbitol | 39.7 | 41.7 | 43.6 | 45.5 |
| Polyethylene glycol 400 | 5.0 | 5.0 | 5.0 | 5.0 |
| Sodium carboxymethyl-cellulose | 1.2 | 1.2 | 1.2 | 1.2 |
| Sodium lauryl sulfate | 1.5 | 1.5 | 1.5 | 1.5 |
| Sodium saccharine | 0.1 | 0.1 | 0.1 | 0.1 |
| Flavour | 1.0 | 1.0 | 1.0 | 1.0 |
| Purified water | 11.6 | 8.7 | 5.8 | 3.0 |
| Total | 100.0% | 100.0% | 100.0% | 100.0% |
| Refractive index of toothpaste | 1.445 | 1.450 | 1.455 | 1.460 |

From the results shown in FIG. 1 and FIG. 2, it is recognized that the zirconosilicate, when compared with the usual amorphous anhydrous silica, shows the less minimum turbidity and is more suitable than the anhydrous silica as the abrasive for preparing transparent dentifrices. Furthermore, while the zirconosilicate shows less fluctuation in the refractive index even when stored at various temperatures and has excellent aging stability, the anhydrous silica shows significant fluctuation in the refractive index and remarkable aging instability. Specifically, in the transparent dentifrice using an anhydrous silica as the abrasive, the refractive index of the anhydrous silica fluctuates during storage to increase the difference in relation with the refractive index of the transparent vehicle, resulting in gradual fall of the transparency. On the other hand, in the transparent dentifrice using the zirconosilicate as the abrasive, since the refractive index of the zirconosilicate scarcely fluctuates during storage, the difference of the refractive index in relation with the transparent vehicle scarcely increases, thereby maintaining the transparent appearance.

[EXAMPLE 3]

Toothpastes having the following formulations using the zirconosilicate having a $ZrO_2$ content of 0.5% by weight based on $SiO_2$, the amorphous anhydrous silica and amorphous aluminosilicate as the abrasive, respectively. They were estimated by the Scheffer's paired comparative method with 60 panelers on every items shown in Table 4 according to the following scores. The results are shown in Table 4.

| Toothpaste composition formulation | |
|---|---|
| Abrasive | 10% |
| 96% Glycerine | 22.0 |
| 70% Sorbitol | 43.0 |
| Polyethylene glycol 400 | 5.0 |
| sodium carboxymethylcellulose | 1.2% |
| Sodium lauryl sulfate | 1.5 |
| Sodium saccharine | 0.1 |
| Flavour | 1.0 |
| Purified water | 6.2 |
| Total | 100.0% |

Score

+2 : excellent
+1 : good
 0 : identical
−1 : poor
−2 : extremely poor

TABLE 4

| Item | Main effect dispersing rate | Average preference | | |
|---|---|---|---|---|
| | | Zircono-silicate | Amorphous silica | Alumino-silicate |
| Dispersibility | 1.64 | 0.15 | −0.02 | −0.13 |
| Sandy feeling | 5.02** | 0.27 | −0.12 | −0.15 |
| Astringency | 8.27** | 0.22 | −0.28 | −0.07 |
| Overall preference | 1.51 | 0.17 | −0.05 | −0.12 |

Note: As the result of F test, meaningful 1% difference were recognized for sandy feeling and astringency.

As the results shown in Table 4, it is recognized that the toothpaste using the zirconosilicate provides satisfactory feelings in use.

[EXAMPLE 4]

The liquid absorption was measured by the following method for the zirconosilicates having various zirconium contents, to obtain the results as shown in FIG. 3.

Measurement of liquid absorption

Anhydrous product obtained from a sample by drying 105° C. for 2 hours to remove adsorbed water was weighed by 1.0 g, which was placed on a glass plate and uniformly mixed with 5 ml of aqueous solution of 42.5% glycerine. The glycerine solution was added little by little through a microburet to the sample and the mixing of the sample and the glycerine solution was carried out so that the sample was infiltrated entirely with the glycerine solution by using a stainless steel spatula. When the sample became granular and further gathered into a hard plaster-like mass but the mixture of the sample and glycerine did not stick to the glass plate, it was determined as the end point and the amount of the liquid required (ml) was determined as the liquid absorption.

As can be seen from the results shown in FIG. 3, the liquid absorption of the zirconosilicate decreases as the zirconium content increases, which suggests that an abrasive having an optional absorption can be prepared with ease by adjusting the zirconium content in the zirconosilicate, to provide a great merit in preparing a dentifrice. On the other hand, in usual amorphous anhydrous silicas not bonded with zirconium, different from the zirconosilicate, it is impossible to adjust the liquid absorption unless the production method is changed and, moreover, it is difficult to optionally produce anhydrous silicas having desired liquid absorption. In order to obtain a desired viscosity in a usual dentifrice based on amorphous anhydrous silica, it can not but change the composition of the dispersant (dentifrice vehicle). On the contrary, in the case of the zirconosilicate, the abrasive with a desired absorption can be produced optionally by varying the zirconium content and, accordingly, a dentifrice having a desired viscosity can be prepared with ease by using a zirconosilicate having a desired absorption, which means that the zirconosilicate has an excellent blendability.

[EXAMPLE 5]

In 24 g of water was dispersed 16 g of abrasive. The resulting dispersion was mixed with 40 g of aqueous solution containing 1000 ppm of fluoride in the form of sodium fluoride (NaF) or sodium monofluorophosphate ($Na_2PO_3F$). The mixture was shaken at 27° C. for 18 hours. The mixture was centrifuged at 10000 rpm for 20 minutes to separate into powder and solution. The concentration of fluoride in the supernatant liquid was measured with a fluoride ion electrode. The results are shown in Table 5.

TABLE 5

| Abrasive | NaF | $Na_2PO_3F$ | pH of 5% slurry |
|---|---|---|---|
| Blank | 625 ppm[*1] | 625 ppm[*1] | — |
| Calcium secondary phosphate dihydrate | 170 | 185 | 7.1 |
| Aluminum hydroxide | 195 | 290 | 8.5 |
| Zirconosilicate[*2] | 605 | 610 | 8.6 |

TABLE 5-continued

| Abrasive | NaF | Na₂PO₃F | pH of 5% slurry |
|---|---|---|---|
| Silica (Sident 5) | — | 570 | 7.5 |

Note:
*¹40/(24 + 40) × 1000 = 625 ppm
*²Properties of zirconosilicate:
Specific surface area: 18 m$^2$/g
Average particle diameter: 7.5 μm
Primary particle diameter: 0.2 μm
Amount of ZrO$_2$: 0.3%

It is noted from Table 5 that zirconosilicate does not react with the fluoride compound used, and that zirconosilicate and the fluoride compound are highly miscible with each other.

[EXAMPLE 6]

In 24 g of water was dispersed 16 g of abrasive. The resulting dispersion was mixed with 40 g of aqueous solution containing 1000 ppm of fluoride in the form of sodium fluoride (NaF) or sodium monofluorophosphate (Na$_2$PO$_3$F). The mixture was shaken at 27° C. for 18 hours. The mixture was centrifuged at 10000 rpm for 20 minutes to separate into powder and solution. 10 g of the supernatant liquid was taken. Into this liquid was dispersed 0.2 g of tooth enamel powder (100 to 200 mesh). The resulting dispersion was shaken in a water bath at 37° C. for 30 minutes. After suction filtration, enamel powder was washed with 500 ml of water, and then with ethanol and finally with acetone, and dried under reduced pressure overnight.

About 0.1 g of the enamel powder was accurately weighed and dissolved in perchloric acid. The concentration of fluoride in the solution was measured with a fluoride ion electrode. From this result was calculated the amount of fluoride which had entered the enamel powder. The amount was regarded as the uptake of fluoride by the tooth enamel. The results are shown in Table 6.

TABLE 6

| Abrasive | NaF | Na₂PO₃F | pH of 5% slurry |
|---|---|---|---|
| Bank | 42 μg/g*³ | 42 μg/g*³ | — |
| Calcium secondary phosphate anhydrous | 103 | 120 | 7.1 |
| Aluminum hydroxide | 98 | 105 | 8.5 |
| Zirconosilicate*⁴ | 180 | 175 | 6.6 |
| Silica (Sident 5) | — | 150 | 7.5 |

Note:
*³Amount of fluorine which is originally contained in enamel powder.
*⁴Properties of zirconosilicate:
Specific surface area: 250 m$^2$/g
Average particle diameter: 7.5 μm
Primary particle diameter: 0.2 μm
Amount of ZrO$_2$: 0.3%

It is noted from Table 6 that zirconosilicate helps increase the uptake of fluoride.

[EXAMPLE 7]

Four kinds of toothpaste were prepared according to the formulation shown in Table 7. After storage at 20° C. for 6 months, the samples were examined for the amount of soluble fluorine and the uptake of fluorine by the tooth enamel. The results are shown in Table 7.

Procedure for determination of soluble fluoride:
(1) Place 2.0 ml of sample in a 20-ml measuring flask, and fill the flask with pure water.
(2) Take a 2.0 mm aliquot, add 2.5 ml of 1M perchloric acid, and further add 0.5 ml of pure water. In case of monofluorophosphate the thus obtained solution is allowed to stand for 24 hours.
(3) Add 15 ml of 0.5M citric acid solution. While stirring, measure the concentration of fluoride ion with a fluoride ion electrode.

Amount of soluble fluorine (ppm)=(Reading of meter)×100

Procedure for determination of uptake of fluorine:

In 27 g of water was suspended 9 g of toothpaste, followed by thorough shaking. The suspension was centrifuged at 10000 rpm for 20 minutes, and 10 g of the supernatant liquid was taken. The liquid was treated as in Example 6 to determine the uptake of fluorine.

TABLE 7

| | No. 1 | No. 2 | No. 3 | No. 4 |
|---|---|---|---|---|
| Stannous fluoride | 0.4% | 0.4% | 0.4% | 0.4% |
| 40% sodium phytate | — | 1.25 | 2.5 | 2.5 |
| Zirconosilicate*⁵ | 28.0 | 28.0 | 28.0 | 28.0 |
| Sodium carboxymethylcellulose | 1.3 | 1.3 | 1.3 | 1.3 |
| Gelatin | 0.3 | 0.3 | 0.3 | 0.3 |
| Glycerin | 20.0 | 20.0 | 20.0 | 30.0 |
| 60% sorbitol solution | 15.0 | 15.0 | 15.0 | — |
| Propylene glycol | 3.0 | 3.0 | 3.0 | 3.0 |
| Sodium lauryl sulfate | 1.5 | 1.5 | 1.5 | 1.5 |
| Lauroyl diethanolamide | 0.5 | 0.5 | 0.5 | 0.5 |
| 20% sodium hydroxide | — | 0.3 | 0.4 | 0.4 |
| Sodium saccharin | 0.1 | 0.1 | 0.1 | 0.1 |
| Flavor | 1.0 | 1.0 | 1.0 | 1.0 |
| Preservative | 0.1 | 0.1 | 0.1 | 0.1 |
| Purified water | Balance | Balance | Balance | Balance |
| Total | 100.0% | 100.0% | 100.0% | 100.0% |
| Amount of soluble fluorine (20° C., 6 months) | 690 ppm | 910 ppm | 945 ppm | 935 ppm |
| Uptake of fluorine | 700 ppm | 880 ppm | 870 ppm | 850 ppm |

*⁵Same as zirconosilicate *² in properties.

It is noted from Table 7 that the activity of fluoride is increased by the combined use of myo-inositol phosphate ester (sodium phytate) and stannous fluoride.

[EXAMPLES 8 TO 10 AND COMPARATIVE EXAMPLES 1 TO 3]

Six kinds of toothpaste were prepared according to the formulation shown in Table 8. The samples were examined for the retention of total soluble fluoride.

"The retention of fluoride" in these examples was obtained by comparing the amount of total soluble fluoride in the samples which had been stored at 25° C. for 3 years with the amount of total soluble fluoride in the initial samples. The determination was carried out in the same way as in Example 7.

TABLE 8

| | Example | | | Comparative Example | | |
|---|---|---|---|---|---|---|
| | 8 | 9 | 10 | 1 | 2 | 3 |
| Zirconosilicate | 40% | 40% | 40% | — | — | — |
| Calcium secondary phosphate dihydrate | — | — | — | 40% | 40% | — |
| Aluminum hydroxide | — | — | — | — | — | 40% |

TABLE 8-continued

|  | Example | | | Comparative Example | | |
| --- | --- | --- | --- | --- | --- | --- |
|  | 8 | 9 | 10 | 1 | 2 | 3 |
| Sodium fluoride | 1.0 | — | — | 1.0 | — | — |
| Sodium monofluorophosphate | — | 1.0 | 1.0 | — | 1.0 | 1.0 |
| Sodium carboxymethylcellulose | 0.9 | 0.9 | 1.2 | 1.0 | 1.0 | 1.2 |
| Propylene glycol | 2.5 | 2.0 | 3.0 | 3.0 | 2.0 | 3.0 |
| Sorbitol solution | 15 | 25 | 45 | 20 | 15 | 20 |
| Glycerin | 20 | 10 | — | 15 | 20 | 10 |
| Sodium saccharin | 0.1 | 0.1 | 0.1 | 0.1 | 0.1 | 0.1 |
| Sodium lauryl sulfate | 1.5 | 1.5 | 1.5 | 1.5 | 1.5 | 1.5 |
| Preservative | 0.1 | 0.1 | 0.1 | 0.1 | 0.1 | 0.1 |
| Flavor | 1.0 | 1.0 | 1.0 | 1.0 | 1.0 | 1.0 |
| Purified water | Balance | Balance | Balance | Balance | Balance | Balance |
| Total | 100.0% | 100.0% | 100.0% | 100.0% | 100.0% | 100.0% |
| Retention of fluorine | 92.0% | 95.0% | 93.0% | 51.0% | 61.0% | 65.0% |

Zirconosilicate in Examples 8 and 9 is the same as that in Example 5 in properties.
Zirconosilicate in Example 10 is the same as that in Example 6 in properties.

What is claimed is:

1. An oral composition comprising:
1 to 50% by weight of the composition of a zirconium-bonded synthetic amorphous silicate with a zirconium content of 0.1 to 10% by weight as $ZrO_2$ based on $SiO_2$ as an abrasive, and a fluoride compound selected from the group consisting of alkali metal fluoride, alkali metal monofluorophosphate and stannous-containing fluoride compound, with a fluoride content of 50 to 10,000 ppm based on the total composition.

2. The oral composition as defined in claim 1, in which the zirconium content of the zirconium-bonded synthetic amorphous silicate is in the range of 0.2 to 2% by weight as $ZrO_2$ based on $SiO_2$.

3. The oral composition as defined in claim 1, which is made transparent by adjusting the refractive index of the zirconium-bonded synthetic amorphous silicate and that of the dentifrice vehicle substantially identical to each other.

4. The oral composition as defined in claim 1, in which the zirconium-bonded synthetic amorphous silicate has a refractive index of 1.40 to 1.47, a specific surface area of less than 800 m²/g, a specific gravity of 1.9 to 2.3, and a glycerine absorption of 0.4 to 2.0 ml/g.

5. The oral composition as defined in claim 1, which further contains a stannous compound and a compound selected from the group consisting of myo-inositol tetraphosphate ester, myo-inositol pentaphosphate ester, myo-inositol hexaphosphate ester and salts thereof.

6. The oral composition as defined in claim 1, wherein the content of the impurities is less than 10% by weight of the zirconium-bonded synthetic amorphous silicate.

7. The oral composition as defined in claim 1, wherein the fluoride content is 200 to 10,000 ppm.

8. The oral composition as defined in claim 1, in which the said composition is a dentifrice composition 9. The oral composition as defined in claim 1, in which the dentifrice composition is a toothpaste.

10. The oral composition as defined in claim 8, which contains a dentifrice vehicle containing an effective stabilizing amount of water, a humectant and an effective amount of a flavoring material.

11. The oral composition as defined in claim 8, which is transparent.

12. The oral composition as defined in claim 8, which is opaque.

13. The oral composition of claim 5, in which the said composition is a dentifrice composition.

14. The oral composition of claim 13, in which the dentifrice composition is a toothpaste.

* * * * *